(12) United States Patent
El-Siblani (10) Patent No.: US 8,003,040 B2
(45) Date of Patent: Aug. 23, 2011

(54) PROCESS AND FREEFORM FABRICATION SYSTEM FOR PRODUCING A THREE-DIMENSIONAL OBJECT

(75) Inventor: Ali El-Siblani, Dearborn Heights, MI (US)

(73) Assignee: Envisiontec GmbH, Gladbeck (DE)

( * ) Notice: Subject to any disclaimer, the term of this patent is extended or adjusted under 35 U.S.C. 154(b) by 1 day.

(21) Appl. No.: 12/290,020

(22) Filed: Oct. 24, 2008

(65) Prior Publication Data

US 2009/0146344 A1    Jun. 11, 2009

Related U.S. Application Data

(60) Provisional application No. 61/000,603, filed on Oct. 26, 2007, provisional application No. 61/067,648, filed on Feb. 29, 2008.

(30) Foreign Application Priority Data

Nov. 5, 2007    (EP) .................................... 07021480

(51) Int. Cl.
*B29C 35/08* (2006.01)
(52) U.S. Cl. .......................... 264/401; 264/460; 425/135
(58) Field of Classification Search .................. 264/401, 264/460; 425/135
See application file for complete search history.

(56) References Cited

U.S. PATENT DOCUMENTS

| | | | |
|---|---|---|---|
| 4,837,379 A | 6/1989 | Weinberg | |
| 4,929,402 A | 5/1990 | Hull | |
| 4,999,143 A | 3/1991 | Hull et al. | |
| 5,093,130 A | 3/1992 | Fujii et al. | |
| 5,137,662 A | 8/1992 | Hull et al. | |
| 5,139,338 A | 8/1992 | Pomerantz et al. | |

(Continued)

FOREIGN PATENT DOCUMENTS

DE    41 05 314    8/1991

(Continued)

OTHER PUBLICATIONS

International Preliminary Report on Patentability for PCT/EP2008/009041, dated Apr. 27, 2010.

(Continued)

*Primary Examiner* — Yogendra Gupta
*Assistant Examiner* — Robert J Grun
(74) *Attorney, Agent, or Firm* — Hansen IP Law PLLC (57) ABSTRACT

The present invention provides a process for producing at least one three-dimensional object, comprising: providing a material to be solidified; delivering electromagnetic radiation and/or synergistic stimulation in a pattern or an image to a building region for solidifying said material; wherein said delivering of electromagnetic radiation and/or synergistic stimulation is performed selectively to a defined area or volume of said material to be solidified; and wherein an energy density of electromagnetic radiation and/or synergistic stimulation is controlled and/or adjusted in a border region of said pattern or image and/or is varied in border regions of patterns or images of different building regions of said material, to have an energy density different from the building region other than said border region(s), wherein the controlling and/or adjustment is dependent on, alone or in combination: (a) intensity of electromagnetic radiation and/or synergistic stimulation delivered to said defined area or volume of said material to be solidified; (b) total shape or contour shape of said defined area or volume of said material to be solidified; (c) size of said defined area or volume of said material to be solidified; and (d) material to be solidified. A device is provided likewise.

18 Claims, 5 Drawing Sheets

U.S. PATENT DOCUMENTS

| | | | |
|---|---|---|---|
| 5,143,663 | A | 9/1992 | Leyden et al. |
| 5,157,423 | A | 10/1992 | Zur |
| 5,171,490 | A | 12/1992 | Fudim |
| 5,173,266 | A | 12/1992 | Kenney |
| 5,174,931 | A | 12/1992 | Almquist et al. |
| 5,236,637 | A | 8/1993 | Hull |
| 5,247,180 | A | 9/1993 | Mitcham |
| 5,248,456 | A | 9/1993 | Evans, Jr. et al. |
| 5,263,130 | A | 11/1993 | Pomerantz et al. |
| 5,268,994 | A | 12/1993 | Keskes |
| 5,289,214 | A | 2/1994 | Zur |
| 5,298,208 | A | 3/1994 | Sibley et al. |
| 5,306,446 | A | 4/1994 | Howe |
| 5,345,391 | A | 9/1994 | Hull et al. |
| 5,360,981 | A | 11/1994 | Owen et al. |
| 5,391,072 | A | 2/1995 | Lawton et al. |
| 5,447,822 | A | 9/1995 | Hull et al. |
| 5,510,077 | A | 4/1996 | Dinh et al. |
| 5,529,473 | A | 6/1996 | Lawton et al. |
| 5,545,367 | A | 8/1996 | Bae et al. |
| 5,569,431 | A | 10/1996 | Hull |
| 5,571,471 | A | 11/1996 | Hull |
| 5,630,981 | A | 5/1997 | Hull |
| 5,651,934 | A | 7/1997 | Almquist et al. |
| 5,653,925 | A | 8/1997 | Batchelder |
| 5,823,778 | A | 10/1998 | Schmitt et al. |
| 5,858,746 | A | 1/1999 | Hubbell et al. |
| 5,891,382 | A | 4/1999 | Almquist et al. |
| 5,894,036 | A | 4/1999 | Tylko |
| 5,902,537 | A | 5/1999 | Almquist et al. |
| 5,945,058 | A | 8/1999 | Manners et al. |
| 5,980,813 | A | 11/1999 | Narang |
| 6,013,099 | A | 1/2000 | Dinh et al. |
| 6,027,324 | A | 2/2000 | Hull |
| 6,048,487 | A | 4/2000 | Almquist et al. |
| 6,051,179 | A | 4/2000 | Hagenau |
| 6,153,034 | A | 11/2000 | Lipsker |
| 6,158,946 | A | 12/2000 | Miyashita |
| 6,171,610 | B1 | 1/2001 | Vacanti et al. |
| 6,280,727 | B1 | 8/2001 | Prior et al. |
| 6,281,903 | B1 | 8/2001 | Martin et al. |
| 6,334,865 | B1 | 1/2002 | Redmond et al. |
| 6,352,710 | B2 | 3/2002 | Sawhney et al. |
| 6,391,245 | B1 | 5/2002 | Smith |
| 6,500,378 | B1 | 12/2002 | Smith |
| 6,547,552 | B1 | 4/2003 | Fudim |
| 6,630,009 | B2 | 10/2003 | Moussa et al. |
| 6,764,636 | B1 | 7/2004 | Allanic et al. |
| 6,833,231 | B2 | 12/2004 | Moussa et al. |
| 6,833,234 | B1 | 12/2004 | Bloomstein et al. |
| 6,942,830 | B2 | 9/2005 | Mülhaupt et al. |
| 6,974,656 | B2 | 12/2005 | Hinczewski |
| 6,989,225 | B2 | 1/2006 | Steinmann |
| 7,052,263 | B2 | 5/2006 | John |
| 7,073,883 | B2 | 7/2006 | Billow |
| 7,133,041 | B2 | 11/2006 | Kaufman et al. |
| 7,195,472 | B2 | 3/2007 | John |
| 7,215,430 | B2 | 5/2007 | Kacyra et al. |
| 7,261,542 | B2 | 8/2007 | Hickerson et al. |
| 7,467,939 | B2 | 12/2008 | Sperry et al. |
| 2001/0028495 | A1 | 10/2001 | Quate et al. |
| 2001/0048183 | A1 | 12/2001 | Fujita |
| 2002/0028854 | A1 | 3/2002 | Allanic et al. |
| 2002/0155189 | A1 | 10/2002 | John |
| 2003/0067539 | A1 | 4/2003 | Doerfel et al. |
| 2003/0074096 | A1 | 4/2003 | Das et al. |
| 2003/0205849 | A1 | 11/2003 | Farnworth |
| 2004/0008309 | A1 | 1/2004 | Yamahara et al. |
| 2005/0023710 | A1 | 2/2005 | Brodkin et al. |
| 2005/0208168 | A1 | 9/2005 | Hickerson et al. |
| 2005/0248061 | A1 | 11/2005 | Shkolnik et al. |
| 2005/0248062 | A1 | 11/2005 | Shkolnik et al. |
| 2005/0288813 | A1 | 12/2005 | Yang et al. |
| 2006/0078638 | A1 | 4/2006 | Holmboe et al. |
| 2006/0192312 | A1 | 8/2006 | Wahlstrom |
| 2006/0239588 | A1 | 10/2006 | Hull et al. |
| 2006/0249884 | A1 | 11/2006 | Partanen et al. |
| 2007/0074659 | A1 | 4/2007 | Wahlstrom |
| 2007/0075458 | A1 | 4/2007 | Wahlstrom et al. |
| 2007/0075459 | A1 | 4/2007 | Reynolds et al. |
| 2007/0075460 | A1 | 4/2007 | Wahlstrom et al. |
| 2007/0075461 | A1 | 4/2007 | Hunter et al. |
| 2007/0077323 | A1 | 4/2007 | Stonesmith et al. |
| 2007/0090568 | A1* | 4/2007 | Teal et al. .................. 264/308 |
| 2007/0120842 | A1 | 5/2007 | Hess |
| 2007/0257055 | A1 | 11/2007 | Scott et al. |
| 2007/0259066 | A1 | 11/2007 | Sperry et al. |
| 2008/0038396 | A1 | 2/2008 | John et al. |
| 2008/0054531 | A1* | 3/2008 | Kerekes et al. ............ 264/401 |
| 2008/0169586 | A1 | 7/2008 | Hull et al. |
| 2008/0169589 | A1 | 7/2008 | Sperry et al. |
| 2008/0170112 | A1 | 7/2008 | Hull et al. |
| 2008/0179786 | A1 | 7/2008 | Sperry et al. |
| 2008/0179787 | A1 | 7/2008 | Sperry et al. |
| 2008/0181977 | A1 | 7/2008 | Sperry et al. |
| 2008/0206383 | A1 | 8/2008 | Hull et al. |
| 2008/0217818 | A1 | 9/2008 | Holmboe et al. |
| 2008/0226346 | A1* | 9/2008 | Hull et al. .................. 399/177 |
| 2008/0231731 | A1 | 9/2008 | Hull |
| 2008/0309665 | A1 | 12/2008 | Gregory, II |

FOREIGN PATENT DOCUMENTS

| | | |
|---|---|---|
| DE | 41 02 257 | 7/1992 |
| DE | 41 25 534 | 2/1993 |
| DE | 93 19 405 | 5/1994 |
| DE | 43 40 108 | 8/1997 |
| DE | 197 27 554 | 1/1999 |
| DE | 299 11 122 | 11/1999 |
| DE | 198 38 797 | 3/2000 |
| DE | 199 29 199 | 1/2001 |
| DE | 100 03 374 | 8/2001 |
| DE | 100 18 987 | 10/2001 |
| DE | 201 06 887 | 10/2001 |
| DE | 699 09 136 | 5/2004 |
| DE | 10 2004 022 961 | 12/2005 |
| EP | 0 250 121 | 12/1987 |
| EP | 0 426 363 | 5/1991 |
| EP | 0 435 564 | 7/1991 |
| EP | 0 466 422 | 1/1992 |
| EP | 0 484 086 | 5/1992 |
| EP | 1 250 995 | 10/2002 |
| EP | 1 250 997 | 10/2002 |
| EP | 1 270 185 | 1/2003 |
| EP | 1 192 041 | 3/2003 |
| EP | 1 156 922 | 6/2003 |
| EP | 1 338 846 | 8/2003 |
| EP | 1674243 | 6/2006 |
| EP | 1 849 587 | 10/2007 |
| EP | 1 880 830 | 1/2008 |
| EP | 1 894 704 | 3/2008 |
| EP | 1 950 032 | 7/2008 |
| EP | 2 011 631 | 1/2009 |
| FR | 2 254 194 | 7/1975 |
| FR | 2 583 334 | 12/1986 |
| FR | 2 634 686 | 2/1990 |
| FR | 2 692 053 | 12/1993 |
| JP | 04371829 | 12/1992 |
| JP | 08192469 | 7/1996 |
| WO | WO 95/11007 | 4/1995 |
| WO | WO-95/15841 | 6/1995 |
| WO | WO-96/00422 | 1/1996 |
| WO | WO-01/00390 | 1/2001 |
| WO | WO-01/12679 | 2/2001 |
| WO | WO-01/72501 A1 | 10/2001 |
| WO | WO-03/059184 | 7/2003 |
| WO | WO-2005/110722 | 11/2005 |
| WO | 2009053100 A1 | 4/2009 |

OTHER PUBLICATIONS

Wohlers Report 2000, "Rapid Prototyping & Tooling State of the Industry Annual Worldwide Progress Report", T. Wohlers, Wohlers Association, Inc., Fort Collins, Colorado (2000).

Stark, G.B., et al., "Biological Matrices and Tissue Reconstruction", Springer Publications, Berlin (1998).

Sachs, E., et al., "Three Dimensional Printing: Rapid Tooling and Prototypes Directly from CAD Model", Journal of Engineering for Industry, 114:481-488 (1992).

Kuhtreiber, W., Ph.D., et al., "Cell Encapsulation Technology and Therapeutics", Birkhauser, Boston (1998).

Landers, R., and Mulhaupt, R., "Desktop Manufacturing of Complex Objects, Prototypes and Biomedical Scaffolds by Means of Computer-Assisted Design Combined with Computer-Guided 3D Plotting of Polymers and Reactive Oligomers," Macromolecular Materials and Engineering, 282:17-22 (2000).

Okada, T., and Ikada, Y., "Tissue Reactions to Subcutaneously Implanted, Surface-Modified Silicones", Journal of Biomedical Materials Research, 27:1509-1518 (1993).

Relou, I.A., et al., "Effect of Culture Conditions on Endothelial Cell Growth and Responsiveness", Tissue & Cell, 30(5):525-538 (1998).

Nikolaychik, V.V., et al., A New, Cryopreciptate Based Coating for Improved Endothelial Cell Attachment and Growth on Medical Grade Artificial Surfaces:, ASAIO Journal, 40:M846-M852 (1994).

Burns, "Automatic Fabrication Improving Productivity in Manufacturing", 1993 (ISBN 0-13-119462-3).

Opposition to EP 1,849,587, dated Apr. 8, 2010.

C. Sun, et al., "Projection Micro-Stereolithography Using Digital Micro-Mirror Dyanmic mask," Sensors and Actuators A 121 (2005) 113-120.

S. Ventura, et al., "Freedorm Fabrication of Functional Silicon Nitride Components by Direct Photoshaping," Mat. Res. Sol. Symp Proc., vol. 625 (2000).

K. Takahashi, "A New Application of DMD to Photolithography and Rapid Protoyping System," Institute of Electronics, Information, and Communication Engineers.

* cited by examiner

PROCESS AND FREEFORM FABRICATION SYSTEM FOR PRODUCING A THREE-DIMENSIONAL OBJECT

FIELD OF THE INVENTION

The present invention relates to a process and a device for producing at least one three-dimensional object by solidifying a solidifiable material. The process and the device are particularly suitable for producing and providing three-dimensional objects with improved border control.

BACKGROUND ART

Known processes and devices for producing at least one three-dimensional object by solidifying a solidifiable material are sometimes referred to as rapid prototyping and manufacturing techniques, and sometimes they are more specifically referred to as stereolithography, laser sintering, fused deposition modelling, selective light modulation and the like, without being limited thereto. In the following, processes, devices and systems of this art are commonly referred to as "freeform fabrication".

For example, EP 1 849 587 A1 discloses a process and a device for producing a three-dimensional object employing s computer unit, an IC and/or a software implementation capable of selectively adjusting and/or controlling energy input into a voxel matrix via a gray level and/or colour level.

Especially in situations affording three-dimensional objects of particular properties formed by freeform fabrication, such as higher strength, the material to be solidified may comprise a filler and a binder.

SUMMARY OF THE INVENTION

The object of the present invention was to provide of a process and a device for allowing to produce a three-dimensional object with higher dimensional accuracy, in particular when a material to be solidified comprises a filler and a binder, and which process or device is further improved in terms of reliability.

In accordance with an aspect, the present invention provides a process for producing at least one three-dimensional object, comprising: providing a material to be solidified; delivering electromagnetic radiation and/or synergistic stimulation in a pattern or an image to a building region for solidifying said material; wherein said delivering of electromagnetic radiation and/or synergistic stimulation is performed selectively to a defined area or volume of said material to be solidified; and wherein an energy density of electromagnetic radiation and/or synergistic stimulation is controlled and/or adjusted in a border region of said pattern or image and/or is varied in border regions of patterns or images of different building regions of said material, to have an energy density different from the building region other than said border region(s), wherein the controlling and/or adjustment is dependent on, alone or in combination:
(a) intensity of electromagnetic radiation and/or synergistic stimulation delivered to said defined area or volume of said material to be solidified;
(b) total shape or contour shape of said defined area or volume of said material to be solidified;
(c) size of said defined area or volume of said material to be solidified; and
(d) material to be solidified.

Likewise, the present invention further provides a freeform fabrication system comprising: a material to be solidified; a electromagnetic radiation and/or synergistic stimulation delivery device capable of delivering electromagnetic radiation and/or synergistic stimulation in a pattern or an image to a building region for solidifying said material; wherein said electromagnetic radiation and/or synergistic stimulation delivery device is designed to selectively deliver electromagnetic radiation and/or synergistic stimulation to a defined area or volume of said material to be solidified; and wherein the freeform fabrication system further comprises a control unit adapted to control electromagnetic radiation and/or synergistic stimulation delivered from a border region of said pattern or image, and/or from border regions of patterns or images of different building regions of said material, for adopting an energy density different from regions other than that border region(s), respectively dependent on, alone or in combination:
(a) intensity of electromagnetic radiation and/or synergistic stimulation delivered to said defined area or volume of said material to be solidified;
(b) total shape or contour shape of said defined area or volume of said material to be solidified;
(c) size of said defined area or volume of said material to be solidified; and
(d) material to be solidified.

In accordance with another aspect, the present invention provides a process for producing at least one three-dimensional object, or for preparing the production thereof, said production process being of a type comprising: providing a material to be solidified; delivering electromagnetic radiation and/or synergistic stimulation in a pattern or an image to a building region for solidifying said material; wherein said delivering of electromagnetic radiation and/or synergistic stimulation is performed selectively to a defined area or volume of said material to be solidified; wherein said production or said preparation process includes the steps of: performing a virtual or actual solidification step, in which the degree of either out-shining electromagnetic radiation and/or synergistic stimulation towards outside regions, or in-shining electromagnetic radiation and/or synergistic stimulation into internal regions respectively across a border region or border regions of a three-dimensional object to be constructed is observed or determined, and adapting the energy density of electromagnetic radiation and/or synergistic stimulation in said border region(s) in response to said observed or determined degree of out- or in-shining across the border region(s).

The solidification step can be carried out virtually by a computer, an IC or by software algorithm, or actually by a test carried out on a test machine.

Likewise, the present invention provides a freeform fabrication system for producing at least one three-dimensional object, or for preparing the production thereof, said freeform fabrication system being of a type comprising: a material to be solidified; a device for delivering electromagnetic radiation and/or synergistic stimulation in a pattern or an image to a building region for solidifying said material, such that said electromagnetic radiation and/or synergistic stimulation is delivered selectively to a defined area or volume of said material to be solidified; wherein said freeform fabrication system is adapted to perform a virtual or actual solidification step, in which the degree of either out-shining towards outside regions, or in-shining into internal regions respectively across a border region or border regions of a three-dimensional object to be constructed is observed or determined, and wherein said freeform fabrication system further comprises a control unit capable of adapting the energy density of electromagnetic radiation and/or synergistic stimulation in said border region(s) in response to said observed or determined degree of out- or in-shining across the border region(s).

In accordance with still another aspect, the present invention provides a process for producing at least one three-dimensional object, comprising: providing a material to be solidified, the material comprising a photocurable resin; delivering electromagnetic radiation or synergistic stimulation in a pattern or an image to a building region for solidifying said material to be solidified; wherein said delivering of electromagnetic radiation and/or synergistic stimulation is performed selectively to a defined area or volume of said material to be solidified by using a mask projector; and wherein an energy density of electromagnetic radiation or synergistic stimulation is controlled or adjusted in a border region of said pattern or image, or is varied in border regions of patterns or images of different building regions of said material to be solidified, to have an energy density different from regions other than said border region(s), wherein the three-dimensional object is built on an object carrier or support, and wherein said object carrier or support is moved upward as the built three-dimensional object grows; and wherein the material to be solidified is conveyed from a resin source to the building region on a movable film.

Likewise, the present invention provides a freeform fabrication system, comprising: a material to be solidified, the material comprising a photopolymer resin; a electromagnetic radiation or synergistic stimulation delivery device based on a mask exposure system or a projection system, capable of delivering electromagnetic radiation or synergistic stimulation in a pattern or an image to a building region for solidifying said material; an object carrier or support movable upward or downward; and a conveyor system for conveying the material to be solidified from a material source to the building region on a movable film; wherein the freeform fabrication system further comprises a control unit adapted to control electromagnetic radiation or synergistic stimulation delivered from a border region of said pattern or image, or from border regions of patterns or images of different building regions of said material to be solidified, for adopting an energy density different from regions other than said border region(s).

The common concept of the invention resides in that each factor (a) to (d) specified above significantly and variably affects the value of energy density either out-shining towards outside regions, or in-shining into internal regions of the three-dimensional object under construction, and the respectively varying effects are compensated by appropriately controlling and/or adjusting the energy density in the respective border region(s).

According to particularly significant situations, the level of the aforementioned out-shining or blooming irradiation is higher respectively relative to a reference value, when in the aforementioned case (a) the intensity is higher relative to a standard intensity, in the aforementioned case (b) the total shape or contour shape has concave portions relative to linear portions or convex portions, in the aforementioned case (c) the size is larger relative to a standard size, and in the aforementioned case (d) the material itself or a component contained in the material to be solidified has a scattering property relative to a non-scattering property or an absorbing property, and therefore the compensating control and/or adjustment is performed by correspondingly lowering the energy density in the border region(s) relative to the standard intensity in case (a), relative to linear or convex portions in case (b), relative to the standard size in case (c), and relative to the use of a non-scattering or absorbing property of the material in case (d), respectively.

In turn, the situations are opposite as specified above when the level of the out-shining or blooming irradiation is lower respectively relative to a reference value, when in case (a) the intensity is lower relative to a standard intensity, in case (b) the total shape or contour shape has convex portions relative to linear portions or concave portions, in case (c) the size is smaller relative to a standard size, and in case (d) the material itself or a component contained in the material to be solidified has an absorbing property relative to a non-absorbing property or a scattering property, and therefore the compensating control and/or adjustment is performed by correspondingly increasing the energy density in the border region(s) relative to the standard intensity in case (a), relative to linear or concave portions in case (b), relative to the standard size in case (c), and relative to the use of a non-absorbing or scattering property of the material in case (d), respectively.

In each of the aforementioned situations, the respective reference value may alternatively also be defined by the energy density in normal non-border area regions/volume regions of the material to be solidified, i.e. other than the border region(s).

Thus, the present invention deals with effects displayed by certain critical factors on blooming, blurring or aberration of electromagnetic radiation and/or synergistic stimulation across border regions in a XY building plane, and thereby enables a new concept of counterbalancing such effects and forming exact dimensional limitations via border brightness control.

The term "border region" used herein means the part of a pattern or image of the electromagnetic radiation and/or synergistic stimulation which, when delivered selectively to a defined area or volume of said material to be solidified, forms a corresponding part of the built three-dimensional object defining the border to non-solidified material. The border region may exist towards an outside space, i.e. towards an external non-built space, and/or towards an inside space, i.e. towards an internal non-built space such as hollow volumes, voids or cavities. The border region to be controlled and/or adjusted may extend exactly to dimensional limits intended to be solidified, or it may purposively exceed such dimensional limits for adjusting the actually solidified surface of the three-dimensional object. The control and/or adjustment in one border region may not only refer to a relation to non-border regions of the same building region, but instead or in addition it may lead to a variation of energy densities present between a border region in one building region and another border region in another building region of the whole built three-dimensional object, i.e. to variations in patterns or images of border regions of different building regions.

The present invention is particularly advantageous in cases where a three-dimensional object is formed from a solidifiable material comprising a filler and a binder by electromagnetic radiation and/or synergistic stimulation according to any one of the above mentioned embodiments. For example, a presence (and possibly a type) or absence of a particulate or fibrous filler substance distinctively affect border regions being particularly relevant for a accurate or differentiated solidification. By the processes and fabrication systems according to the present invention, a three-dimensional object having an improved combination of product characteristics is obtained, in particular a homogenous mechanical strength throughout the object (albeit being formed by an additive generative process) combined with a high dimensional accuracy.

Principles, advantages and preferred embodiments will be described in further detail below.

BRIEF DESCRIPTION OF THE DRAWINGS

The present invention will be described in more detail by referring to preferred embodiments, examples and figures, which are however for illustrative purposes only and shall not be understood in a limiting manner, wherein.

DESCRIPTION OF PREFERRED EMBODIMENTS

In accordance with the present invention, it has been found that solidification behaviour in those parts of areas or volumes of a building region, which correspond to the border regions, is critically affected by characteristics (a) to (d) mentioned above. Mechanisms affecting relevant process and product characteristics can be well adjusted according to the present invention by actively and selectively controlling energy density delivered by the electromagnetic radiation and/or synergistic stimulation (also known as "exposure energy density", measured in a unit of $J/m^2$ or $mJ/cm^2$ or $mW/dm^2$, in the following briefly denoted "energy density"). With the energy density being at least partially varied across border regions, it is possible to produce three-dimensional objects having well-balanced counter-acting properties such as homogeneous mechanical strength and high dimensional accuracy, i.e. avoiding local distortions that may be caused by a differential influence of aforementioned characteristics (a) to (d). In accordance with the present invention, control and/or adjustment of energy density across a border region, or variation of energy densities between different border regions means that at least in part(s) of an exposed pattern or image or at least in part(s) of different building regions respectively covered by border regions, there is an active spatial modification of an energy density relative to an unmodified/unvaried exposure. Assuming a building region being defined by a selectively exposed area or volume with dimensions of X, Y and Z relative to the whole built volume of a three-dimensional object to be formed, control and/or adjustment of energy density in a border region is primarily imposed in the projected pattern or image in XY plane. Alternatively or in addition to this, variation of energy densities in different border regions of correspondingly different building regions of the material to be solidified may be imposed.

The aforementioned significant characteristics, depending on which control and/or adjustment can be effectively carried out, will be further explained in the following. When referring to the attached drawings, defined areas of the material to be solidified, in which areas electromagnetic radiation and/or synergistic stimulation are selectively delivered, are shown by weight areas, and varying values of energy densities outshining towards outside regions are indicated by grayish shadows surrounding these defined areas.

Figure 1:
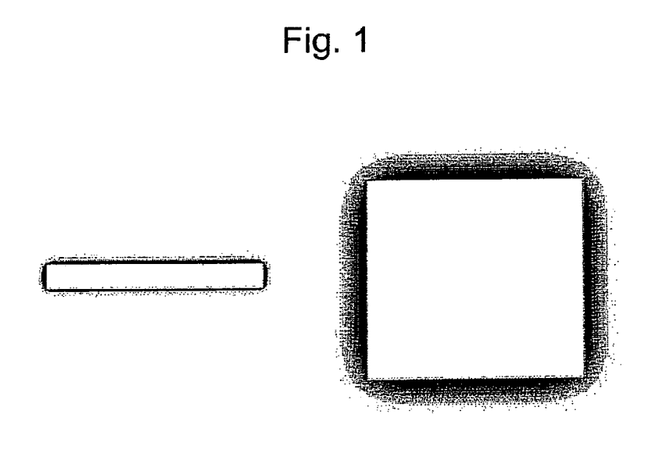
FIG. 1 schematically shows a principle of the present invention by referring to effects of type (a) of varying intensities of irradiation, type (b) of varying total shapes, and type (c) of varying sizes of defined area or volume of material to be solidified.

(a) Intensity of Electromagnetic Radiation and/or Synergistic Stimulation Delivered to a Defined Area or Volume of the Material to be Solidified:

FIG. 1A and FIG. 1B illustrate the distinguishing effects caused by different intensities of electromagnetic radiation and/or synergistic stimulation. As the intensity delivered to a square cross-sectional plane shown by the weight area in FIG. 1B is higher than the intensity delivered to the rectangular cross-sectional plane shown by the weight area in FIG. 1A, the value of energy density out-shining towards outside regions is higher in FIG. 1B than in FIG. 1A (illustrated by respective darkened "shadows" towards the outside of the irradiated areas), and therefore the different effects need to be compensated by appropriately controlling and/or adjusting the energy density in the respective border region(s). Thus, according to the present invention, the border region(s) of the area of FIG. 1B are controlled to deliver an energy density lower than the non-border inside region of the square area, for example by gray level allocation of border pixels relative to weight pixels of a corresponding square bitmap. The border region in case of FIG. 1A is also reduced in energy level delivery relative to the non-border inside region (here of the rectangular area), but by an extend less than in the case of FIG. 1B.

Generally, a reference intensity can be nominally set, and depending on the deviation of an actually used intensity, the energy density in the border region(s) is adjusted, i.e. if the intensity is higher (or, visa versa, lower) than the reference, energy density in the border region is decreased (increased) relative to a reference value.

(b) Total Shape or Contour Shape of Said Defined Area or Volume of Said Material to be Solidified:

The degree of out-shining or blooming is also influenced by the total shape of the defined area or volume utilized for solidification. The degree is higher, the larger the cross-sectional shape per unit area. For example, this degree increases in the following order of total shapes: line/stripe, triangle, rectangle, square, polygonal with increasing polygon number, and circle. This tendency becomes apparent from a comparison between FIG. 1A (rectangle) and FIG. 1B (square) also. According to the present invention, the border regions of a square cross-sectional area can thus be "darkened" in energy delivery compared to a rectangular cross-sectional area, or, more generally, relative to the border region of a reference cross-sectional shape.

As to the contour shape criterion, both FIGS. 1A and 1B demonstrate (as illustrated again by the differently darkened outside "shadows") a lower degree of out-shining or blooming at respective corners compared to side edges. Hence, a corresponding control can be further accomplished depending on whether the border region is at a corner or at a side edge, leading to a relative lower decrease in energy density delivery in the former case than in the latter case, relative to normal non-bonding regions as a reference. This example also shows that a pattern or image of the electromagnetic radiation and/or synergistic stimulation may include multiple distinctively controlled border regions.

Figure 2:
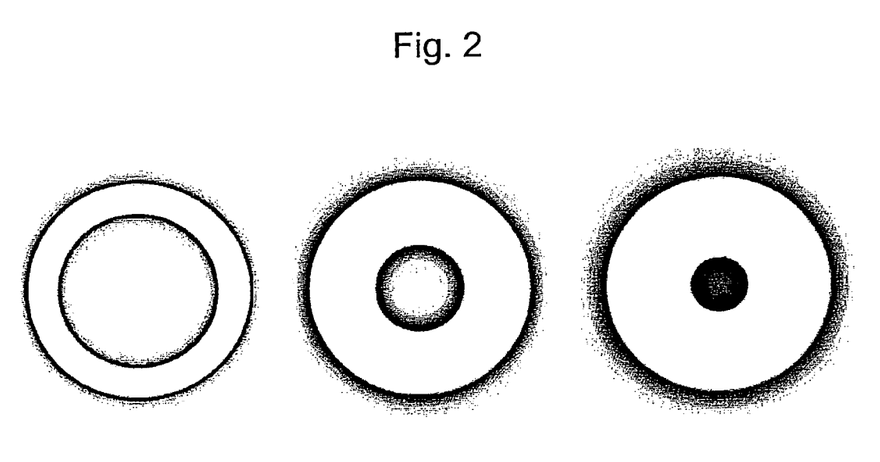
FIG. 2 schematically shows a principle of the present invention by referring to effects of type (a) with other varying intensities of irradiation, type (b) with other varying total shapes and with varying contour shapes, and type (c) with other varying sizes of defined area or volume of material to be solidified FIG. 3 schematically shows a principle of the present invention by referring to a complex situation of varying effects caused by type (b) of varying total shapes and contour shapes.

Further embodiments of control and/or adjustment depending on total shape or contour shape are shown for circular shaped cross-sectional areas in FIGS. 2A, 2B and 2C. As can be clearly seen, out-shining and blooming is stronger at convex contours, i.e. at the inner ring or hole of the ring-shaped cross-sectional area, versa concave contours appearing a the outer edges and contours. The former thus calls for a stronger decrease in energy density (e.g. by gray level control or other energy density adjustment) in the border region than the latter, respectively relative to a reference contour. In this case, a reference may for example be defined by a linear contour. As further apparent from the series in FIGS. 2A-2C, the smaller the inner hole, the higher the out-shining/blooming and thus the stronger control by energy density lowering in the border region is needed for compensation. Generally, radii of inner holes and of outer circles are indicative for the degree of out-shining and blooming and thus can be used as a factor for border brightness control.

(c) Size of Said Defined Area or Volume of Said Material to be Solidified:

In a given unmodified fabrication system, the presence of larger exposure areas or volumes causes a higher blooming or our-shining across and over a border region, relative to smaller or more delicate exposure areas or volumes. For example, this becomes also apparent from a comparison of FIGS. 2A, 2B and 2C: the larger the ring-shaped area, the higher the degree of out-shining both towards the outside space and towards the inner space of the ring (respectively indicated by increasingly darkened "shadows"). The aforementioned tendency may be particularly affected by the presence of filler in the exposed areas or volumes. Therefore, according to the present invention, the larger cross-sectional size of an area or volume of a building region, the more shall the energy density in the border region be controlled or adjusted to lower levels relative to a standard energy density in the non-border regions, and visa versa the smaller the cross-sectional size, the more is the control or adjustment to a relatively higher energy density.

Figure 3:
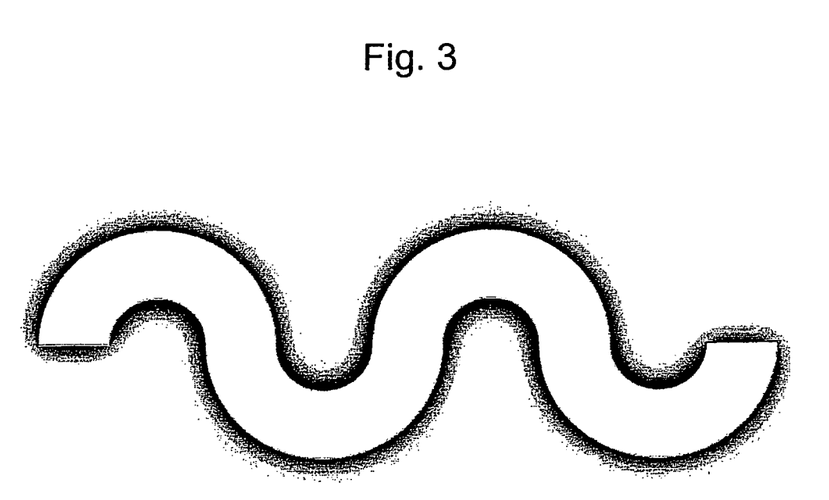

FIG. 3 shows an example of the presence of a complex mixture of convex and concave contour curvature lines interrupted by corners and linear lines, which complexity requires a combination of corresponding adjustments of energy densities in respective border regions based on the above description. Here, the degrees of curvature are indicative for the degree of out-shining and blooming and thus can be used as factors for border brightness control.

(d) Material to be Solidified:

Delivery of electromagnetic radiation and/or synergistic stimulation to boundary regions as opposed mass area or volume regions of the three-dimensional object to be formed are subject to significantly differing characteristics in terms of absorption, reflection and/or scattering performances, as well as in terms of shrinkage performances. Roughly, these characteristics are affected relatively isotropically within area or volume regions, but relatively anisotropically at boundary regions caused by the then present edges.

An example may be explained in case of using a ceramic filler material having reflective and scattering characteristics: Given a certain amount of energy or energy density necessary to solidify the binder of the material in area or volume regions at a desired hardening depth, which hardening depth typically extends into a previously solidified material, a relatively lower amount of energy or energy density is delivered in the boundary regions according to the present invention, thereby counter-balancing size inaccuracies caused by reflection and scattering phenomena in the boundary regions. The opposite may occur in case of using absorbing filler such as carbon black.

Further influencing factors relating to characteristics of the material to be solidified include the following:

(i) Type and/or Amount of Filler Contained in a Material to be Solidified:

For example, depending on whether or to which extent the filler absorbs, reflects, or scatters electromagnetic and/or synergistic radiation, an energy density distribution corresponding to a border region is particularly affected. For example, the more a solidifying material or a component thereof scatters, the higher is an energy density out-shining or blooming outside an actually defined built area or built volume, and hence the border region(s) in this case is reduced in energy density delivery, for example by darkening through gray level gradation of corresponding parts of a bitmap relative to other parts of the bitmap corresponding to non-border regions, in order to achieve a beneficial a compensation control. Conversely, in cases of a material to be solidified where absorption phenomena prevail over reflection or scattering phenomena, energy density should better be increased in border regions relative to inner, non-border areas. Whether absorption or reflection/scattering phenomena prevail may, inter alia, depend on the type of filler. Therefore, the active control or variation of energy density according to the present invention enables an adaptation to the use of a wide variety of different filler substances, including but not limited to ceramics, glass, carbon black, solid polymer particles, metals, metal alloys as described in further detail below, and including modified forms such as making absorptive metal particles reflective by means of suitable coatings, e.g. by waxes, coupling agents, polymers and the like. The present invention also allows to take account of the size and/or the amount of a filler substance being present in a particulate (or powder) or fibrous form, as well as to respond to situations such as filler sedimentation during the fabrication process. Moreover, the present invention provides an advantage that a three-dimensional object can be more reliably produced by using two or more different materials to be solidified, among which at least one comprises a filler, yet with one fabrication system while making use of adapted varied energy density.

(ii) Type and/or Amount of Binder:

Likewise, in combination with the specific type and/or amount of filler substance, critical solidification criteria including absorption, reflection and/or scattering phenomena can be actively influenced depending on the type and/or amount of binder with respect to a certain location within a building region.

(iii) Hardening Rate, Viscosity and/or Flowability of the Material to be Solidified:

Hardening rate, viscosity and/or flowabiltiy behaviour of the material to be solidified can be strongly different dependent on whether a border region or non-border region is concerned. For example, it may be critical whether the material is in a liquid, fluid, thixotropic, semi-solid, paste, high-viscous, medium-viscous and low-viscous state, but behaves differently in respective built areas corresponding to border or non-border regions. Also, these states may vary depending on the status and point of time within the whole building process of a three-dimensional object, or may vary between different building areas or regions, or may vary between different first and second solidifyable materials used in a whole building process. Moreover, brightness level and/or time to sufficiently harden in areas or volumes corresponding to border regions may substantially vary relative to other regions.

The present invention allows for an effective adaptation to each of such varying states by a corresponding preset adaptation or an in-situ control of the energy density in one or more border regions concerned.

In the performance of the present invention, a controlled variation of energy density for the afore-mentioned situations (a) to (d), and specifically for situations (i) to (iii) or for other situations, can be determined and ascertained by theoretical considerations, or by practical experience. A practical testing or verification is preferred in cases where a fabrication system is adapted to the use of a yet unexperienced material to be solidified, or adapted to the use of a new or specific production device. Hence, by testing one or more parameters discussed above, the effects of varied energy density and in particular a selective overexposure or underexposure in at least a part of border regions, or between patterns or images of different building regions, can be readily measured. This allows for a more accurate adjustment depending on the individual building parameters in the whole fabrication process, such design of a particular three-dimensional object to be formed, filler and/or binder contained in the used material, etc. The necessary or desired adjustments can be made in one or more bitmaps. The bitmaps may be generated in advance of a building process, or they may be generated during an ongoing building process "on the fly". Performance of an adaptation step "on the fly" during a production job is particularly efficient and preferred. Moreover, the control may be performed by reference to a standard energy density being defined by any characteristic selected from a reference intensity, a reference total shape, a reference contour shape, a reference size and a reference material, and by adjusting the actual energy density delivered to the border region(s) depending on a variation of actual built data or actual built object relative to said referenced characteristic.

The selective delivery of electromagnetic radiation and/or synergistic stimulation suitably includes an appropriate source capable of electromagnetic radiation and/or synergistic stimulation emission sufficient to solidify the material to be solidified. Solidification by electromagnetic radiation and/or synergistic stimulation according to the present invention may be understood as a process of solidification without photoreaction, such as gelation, fusion and/or sintering, but more preferably is understood as a process of gelation and/or solidification by photoreaction or by thermal setting reaction. Accordingly, the binder may be selected from the group consisting of inert binding agents; adhesives, which may gel, solidify or cure without photoreaction or with photoreaction; and photopolymers or radiation sensitive resins, which may gel and/or solidify by photoreaction and which normally include photopolymerization, cross-linking and/or network formation processes. Besides such a binder (first binder) being solidifyable or curable by the selective delivery of electromagnetic radiation and/or synergistic stimulation, a further binder (second binder) unaffected by such electromagnetic radiation and/or synergistic stimulation or affected by a electromagnetic radiation and/or synergistic stimulation but a modified one (e.g. at a different wavelength or intensity) may be used in addition.

The device for selective delivery of electromagnetic radiation and/or synergistic stimulation further preferably comprises a mask and/or a projection unit to deliver the electromagnetic radiation and/or synergistic stimulation selectively to the defined area or volume of material to be solidified. Electromagnetic radiation and/or synergistic stimulation can be delivered to the building region or parts thereof by means of further suitable components, including but not limited to optical elements, lenses, shutters, voxel matrix projectors, bitmap generators, mask projectors, mirrors and multi-mirror elements and the like. Examples of suitable radiation techniques to selectively deliver electromagnetic radiation and/or synergistic stimulation include, but are not limited to spatial light modulators (SLMs), projection units on the basis of Digital Light Processing (DLP®), DMD®, LCD, ILA®, LCOS, SXRD, etc., reflective and transmissive LCDs, LEDs or laser diodes emitted in lines or in a matrix, light valves, MEMs, laser systems, etc. Use of DLP mask projector is preferred.

The solidifiable material is subjected to selective delivery in a defined area or volume when placed in or on a suitable carrier or provider. Suitable examples for a solidifiable material carrier/provider to be used in the present invention include, but are not limited to a container or vat containing the solidifiable material, or a flexible and/or clear and/or resilient film/foil conveying the solidifiable material. When embodied as a film, the material may then be transferred by suitable film transfer techniques before, during or after the solidification step. Larger volumes of solidifiable material may be stored and supplied from a reservoir or a solidifiable material cartridge to be conveyed to the solidifiable material provider.

Further, the growing and continuously or discontinuously built three-dimensional object may be carried on a suitable carrier or support. The object carrier/support is normally movably arranged in the fabrication system to allow a spatially controlled relationship with the material to be solidified. Alternatively or in combination therewith, the solidifiable material carrier/provider may be arranged movably in a spatially controlled relationship with the object carrier/support (and thus with previously solidified object). Various modifications are feasible when applying the principle of the present invention.

The source for delivery of electromagnetic radiation and/or synergistic stimulation and further optical elements as described above can be arranged relative to the material to be solidified as well as its provider and/or carrier in various suitable ways. For example, the arrangement may be such that electromagnetic radiation and/or synergistic stimulation is delivered from above the building region or the solidifiable material carrier/provider (in which case a carrier for carrying the produced three-dimensional object is usually placed below the building region or a solidifiable material carrier/ provider), or one where electromagnetic radiation and/or synergistic stimulation is delivered from below the building region or a solidifiable material carrier/provider (in which case the carrier for carrying the produced three-dimensional object is usually placed above the building region or a solidifiable material carrier/provider). Again, various modifications are feasible.

A building region may be formed, for example, by a building plane/area or a building volume with desired dimensions in X, Y and Z directions. A building area may be flat, but is not necessarily flat. Further, building regions may be formed as layers, as cross-sections, as a matrix such as a point matrix, a line matrix and especially a voxel matrix, or in any other forms. A desired three-dimensional object can eventually be formed by an additive generative process involving successive solidification of the material in respective building regions.

According to the present invention, energy density can be delivered to the exposure pattern or image, and/or patterns or images of different building regions of the material to be solidified, in various ways or means. To make a variation of energy density efficient and controllable, the selective delivery of electromagnetic radiation and/or synergistic stimulation is preferably based on an imaging unit comprising a predetermined number of discrete imaging elements or pixels, and the control or variation of energy density in the border region(s) is performed by controlling the discrete imaging elements or pixels in a selective manner. Such exposure systems are particularly suitable for the freeform fabrication method of stereolithography.

According to the present invention, energy density of the electromagnetic radiation and/or synergistic stimulation can be controlled or varied in one or more border regions by suitable ways or means. Particularly preferred ways or means include, alone or in combination, the following:

(aa) Various exposure times within the dimensions of XY, XZ, YZ or in Z direction of one or more building regions. For example, this can also be accomplished by using selective shutters with appropriate timings, or selective mask exposures.

(ab) Number of multiple exposures of at least parts of a pattern or an image, or of a pattern or image of at least one among different building regions, respectively covering border regions of concern.

For example, this can be performed by applying multiple mask exposures of a certain cross-sectional area or other building regions of the three-dimensional object to be formed, wherein parts of the respective multiple masks preferably overlap for respective overexposure in corresponding non-border regions and underexposure in corresponding border regions.

(ac) Gradation of energy density in border regions of the exposed pattern or image, or between border regions of different building regions.

This can be most efficiently performed by allocating certain gray values or colour values to corresponding parts of a border region, or to one among the plurality of border regions. The parts allocated by gray or color values are correspondingly underexposed relative to full bright values, yet overexposed relative to black values. Gray value or color value allocation is most efficiently made pixel-wise in a pixel matrix. Since gradation of energy density combines ease of processing with the achievement of high accuracy, especially in the use of filler-containing materials to be solidified, this embodiment is preferably applied, alone or in combination with other variation means.

(ad) Applying a second source or a second delivery of electromagnetic and/or synergistic radiation. For example, the second source or second delivery of electromagnetic radiation and/or synergistic stimulation may be accomplished by a dual or multiple illumination system including the use of two or more radiation sources having respectively same or different wavelengths. In this embodiment, the second or further illumination source may be directed selectively to non-border regions of a pattern or image that need to be overexposed as opposed to border regions. Alternatively, a general infrared (IR) heating source may be used for the general delivery of a basic energy density, while a specific source for delivering electromagnetic radiation and/or synergistic stimulation active for solidifying the material is applied selectively to non-border regions that need to be exposed by additional energy density relative to a selected border region. The first and the second or further sources or deliveries of electromagnetic radiation and/or synergistic stimulation may be located on the same side or on different sides relatively to the building region(s). Further, the deliveries of first and second or further electromagnetic and/or synergistic radiations may be respectively oriented in the same direction or in different directions.

Any variations or combinations of the above variation embodiments are possible and feasible for a person skilled in the art.

A filler which may be mixed with a binder for providing a material usable according to the present invention typically is a solid or substantially solid substance and may include, without being limited to: a ceramic substance such as e.g. alumina, magnesia, zirconia, ceramic oxides of other transition metals such as titania, hafnium oxide, rare earth metal oxides, spinel type double metal oxide ceramics, or mixtures thereof; cermets; silicate, aluminosilicate, apatite, fluoroapatite, hydroxylapatite, phosphates such as tricalcium phosphate, calcium magnesium phosphate, calcium ammonium phosphate, mullite, spinels, and mixtures thereof; glass materials, such as silicate glass, borsilicate glass, quartz glass and mixtures thereof; carbon black; pigments; metals and metal alloys such as stainless steel, titanium or titanium alloy, nickel alloy, copper or copper alloy such as brass (70% copper and 30% zinc), aluminium or aluminium alloy, iron or iron alloy and mixtures thereof; solid polymers or polymer blends such as polymerized acrylic resins and blends or copolymers thereof like polyurethane/polyacrylates, acrylonitril/butadien/styrene-polymerisates (ABS), epoxides and copolymers thereof, nylon and blends or copolymers thereof, polyamid elatomers and mixtures thereof, and other filler substances. In a preferred embodiment, which is particularly beneficial for dental applications in terms of achieving high mechanical strength at good homogeneity combined with high size accuracy (especially when the process includes post-treatment such as sintering and thereby a transformation from a first to a second circumferential size), the filler substance is a ceramic powder, preferably a powder comprising ceramic materials selected from alumina, zirconia, or a mixture thereof. A particularly preferred ceramic powder comprises a ceramic material selected from monoclinical or non-monoclinical zirconia, yttria-doped or -stabilized tetragonal monoclinical or non-monoclinical, single or non-single phased zirkonia (i.e. $ZrO_2$ containing 3-5 mol-% $Y_2O_3$), especially 3YTZP.

The filler component may further comprise one or more kinds of additives, for example but not limited to dispersants, coloring agents such as pigments, post-treatment auxiliary additives such as sintering aids or stabilizers, etc.

The filler may co-fuse or co-sinter itself under the action of electromagnetic radiation and/or synergistic stimulation used for solidification (e.g. especially when polymer fillers are used). It is on the other hand preferred that the filler itself is inert with respect electromagnetic radiation and/or synergistic stimulation at a level which solidifies the binder admixed with the filler, but may nevertheless co-fuse or co-sinter in a post-treatment described later (e.g. when ceramics, glass or metals/metal alloys are used).

The filler may be in the form of particles, a powder, fibers, a net, a scaffold, and the like. The particularly preferred particulate form of the filler is a powder having a suitable particle size, preferably being spherical or essentially spherical in shape, and further preferably having a mean particle size in a range of about 0.001 µm to 100 µm, more preferably in a range of about 0.01 to 50 µm and particularly in a range of about 0.1 to 10 µm. As to the distribution of the absolute particle size of the filler, it may range from about 1 nm to 1000 µm or higher, more preferably from about 0.1 µm to 100 µm. The filler may have a monomodal, a bimodal or a trimodal size distribution, using the same or different filler materials.

The binder substance for the material to be solidified according to the present invention is suitably selected from substances which may themselves lead to solidification of the composite material upon exposure to electromagnetic and/or synergistic radiation. A thus selected binder may not necessarily solidify through photoreaction, but through other mechanisms such as gelation, or it may solidify by chemical reaction after activation through electromagnetic and/or synergistic radiation, possibly together with other co-reactants. Suitable examples of this type of binder are adhesives, including but not limited to waxes and modified waxes, thermally setting resins such as epoxies, and the like. The adhesive properties of adhesives can may be exerted not before solidification of the material to be solidified, and thereby allows partial structures such as layers, strands, dots or other structures or scaffolds, which contain a particulate or fibrous filler, to be successively attached together and to thereby build the three-dimensional object, even without performing a photo-curing reaction.

According to a preferred embodiment, the binder contains at least one selected from photopolymers and thermally hardened resins, in particular a photopolymer which is hardened when subjected to electromagnetic radiation and/or synergistic stimulation of interest. Accordingly, a photopolymer to be used as a binder material may include, but is not limited to: acrylate and/or methacrylate containing compounds, for example mono-, di-, tri-, tetra-, pentaacrylate, such as alkyl- or alkoxy-(meth)acrylates, (meth)acrylic esters having short or long chain alkyl ester groups, e.g. alkyl glycol di(meth) acrylate; epoxy group containing compounds; vinyl group containing or vinyl ether group containing compounds; polysiloxanes; and the like, as well as mixtures thereof. Alternatively, a thermal hardening polymer substance such as an epoxy group containing compound may be used, which is preferably protected with an amine group that decomposes in response to light and/or heat.

The composite material to be solidified according to the present invention may contain further auxiliary agents, including but not limited to: photoinitiators, which may be selected depending on the desired wavelength of electromagnetic and/or synergistic radiation, such as 2-benzyl-2-dimethylamino-1(4-morpholino phenyl)butanone, 1,2,2'-dimethoxy-2-phenylacetophenol, bisimidazoles, benzophenones, α-aminoketones, xanthenes, fluorenes, fluorones, ferrocenes, and the like; co-initiators and/or activation agents such as thioxanthones (e.g. isopropyl thioxanthonel-chloro-4-propoxythioxanthone), 4-benzoyl-4'-methyldiphenyl sulfide, ethyl-p-dimethylaminobenzoate, N,N-dialkyl-toluidine or -aniline, benzophenones, diaryliodo compounds, borates, phosphites, and the like; rheology adjusting agents; viscosity adjusting agents; diluents; solvents; colorants such as dyes and/or color pigments; thixotropic agents; thickeners; stabilizers; coupling agents; welting agents; dispersants; lubricants; adhesives; pore forming agents; and the like, respectively alone or in combination.

The material to be solidified may be provided in a suitable form, including but not limited to liquid, fluid, thixotropic, semi-solid, paste, high-viscous, medium-viscous and low-viscous materials. Preferably but in no way limiting, it has viscosity in the range of about 0.1 Pa·s to $5 \times 10^3$ Pa·s, preferably about 0.2 to about $1 \times 10^3$ Pa·s, more preferably 1 Pa·s to 200 Pa·s, and in particular 10 Pa·s to 100 Pa·s, respectively measured at 25° C.

If a filler is used, a content thereof in the whole material to be solidified suitably lies in a range of about 0.5% by weight to 99.9% by weight, preferably about 1% by weight to about 99% by weight, and more preferably 10% by weight to 85% by weight, particularly above 50% by weight to 85% by weight, and still further preferred 70% by weight to 80% by weight.

After solidification, the three-dimensional object thus produced may be subjected to one or more post-treatments. Suitable post-treatments are selected from post-hardening, de-binding, fusing and sintering, alone or in combination.

Figure 4:
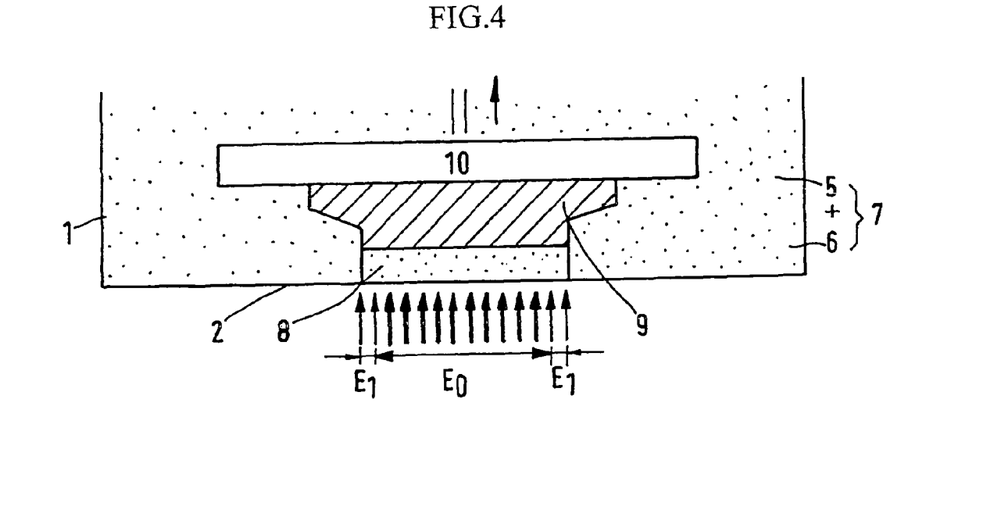
FIG. 4 schematically shows a principle of the present invention by referring to a particular embodiment of a freeform fabrication system where energy density of electromagnetic radiation and/or synergistic stimulation is varied within a pattern or image in XY plane.

According to FIG. 4, in a particular embodiment of a process and a system of freeform fabrication for producing a three-dimensional object based on stereolithography technique, there is used a container or vat 1 for providing a material 7 to be solidified, the material 7 comprising a particulate filler 6 such as yttria stabilized tetragonal zirkonia phase (3YTZP) and a binder 5 such as an acrylate resin. The material 7 to be solidified may contain further constituents as described above, such as a sintering aid in the filler substance and a photoinitiator in the binder, and optionally further auxiliary agents. FIG. 1 shows a process and a system at a certain moment during performance, where a part 9 of a desired three-dimensional object has already been produced and is carried on a three-dimensional object carrier/provider 10, illustrated here in the form of a platform. A gap is formed between the surface of previously solidified partial object 9 and a bottom 2 of the container or vat 1 by an upward movement of three-dimensional object carrier/support 10 (indicated by an arrow at three-dimensional object carrier/support stem). By this upward movement, material yet to be solidified fills the gap, such that the material 7 to be solidified is provided in a desired building region 8. The bottom 2 of vat or container 1 is transparent or transmissive to electromagnetic radiation and/or synergistic stimulation to be used for solidification, at least in a functional part of the bottom.

Within an area defined by XY or a corresponding volume extending in Z direction to thereby specifically define the desired building region 8, electromagnetic radiation and/or synergistic stimulation is selectively delivered as indicated by parallel arrows from below the bottom 2 of vat 1. Here, an exposed energy density is controlled in boundary regions of a corresponding exposure pattern such that, based on a prevailing reflecting and scattering nature of a metal powder filler as filler substance 6, exposure energy density $E_1$ in the boundary region is adjusted lower than energy density $E_0$ applied in the inner area region. Control of energy density can be effected by allocating gray level to the boundary regions of a mask exposure system, relative to an ungraded, bright exposure level of the mask in the inner area region.

Conversely, modifying the fabrication system by using a prevailing absorbing filler substance, energy density variation can be modified in a different manner (not shown) such that higher energy density ($E_1'$) can be exposed in boundary regions, whereas relatively lower basic energy density ($E_0'$) can be exposed to the remaining inner area except the boundary margins.

In this manner, the freeform fabrication system can be adapted and adjusted to the use of a specifically used material containing a filler substance. Moreover, given a predetermined system, accuracy, shrinkage control and homogeneous mechanical strength can be significantly improved by the differential control with respect to boundary regions and large structural area regions, respectively.

Similar control mechanisms can be used in modified embodiments when energy density is desired to be adjusted to a lower level ($E_1$) in the boundary regions relative to a reference standard level ($E_0$) applied in the inner area region depending on (a) total shape or contour shape of said defined area or volume of said material to be solidified, or (b) size of said defined area or volume of said material to be solidified. For example, the difference between $E_0$ and $E_1$ (e.g. accomplished by respectively graded gray level allocation to border regions associated with $E_1$) is adjusted to become relatively smaller when building region 8 has a convex contour line (relative to a reference case which would apply when the contour is a straight linear line), or when the building region 8 covers a relatively small cross-sectional area (relative to a reference building region size). Conversely, the difference is adjusted to become relatively greater in case of a concave contour line of building region 8, or in case of a relatively large cross-sectional area, respectively compared to the reference situations. These modifications can be applied independent of the used material, e.g. also when the material to be solidified does not contain a filler substance.

Figure 5:
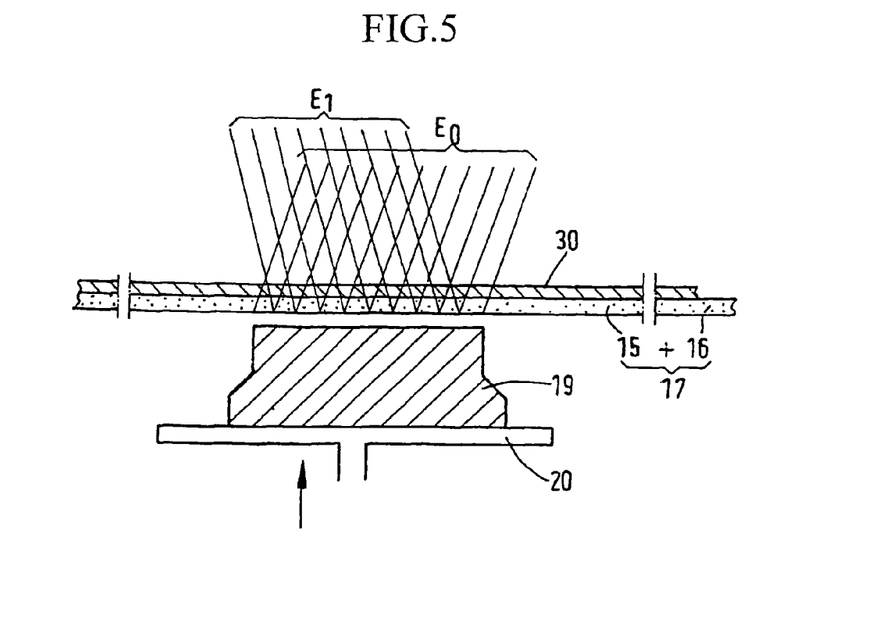
FIG. 5 schematically shows a principle of the present invention using a freeform fabrication system on the basis of a transparent film that carries material to be solidified according to another embodiment, and wherein varied energy density is achieved by superimposing electromagnetic and/or synergistic radiations from different delivery sources.
Figure 6A:
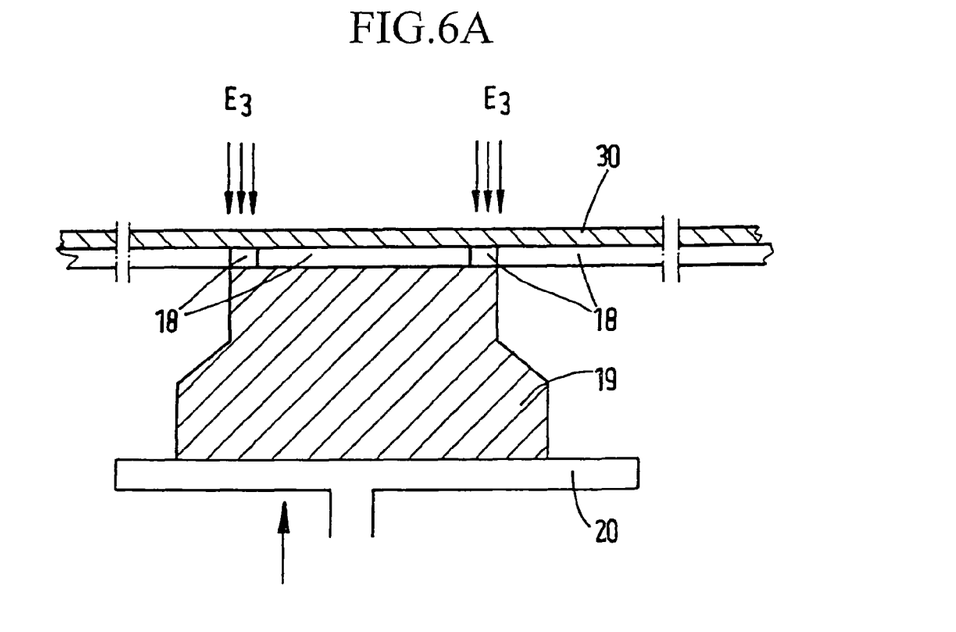
FIGS. 6A and 6B schematically show a principle of the present invention according to another embodiment, wherein different building regions are formed by varied energy densities, respectively, involving building region(s) with a first, filler-containing material to be solidified and one or more other building region using a second, different material to be solidified, wherein the different building regions are associated with correspondingly different energy densities.
Figure 6B:
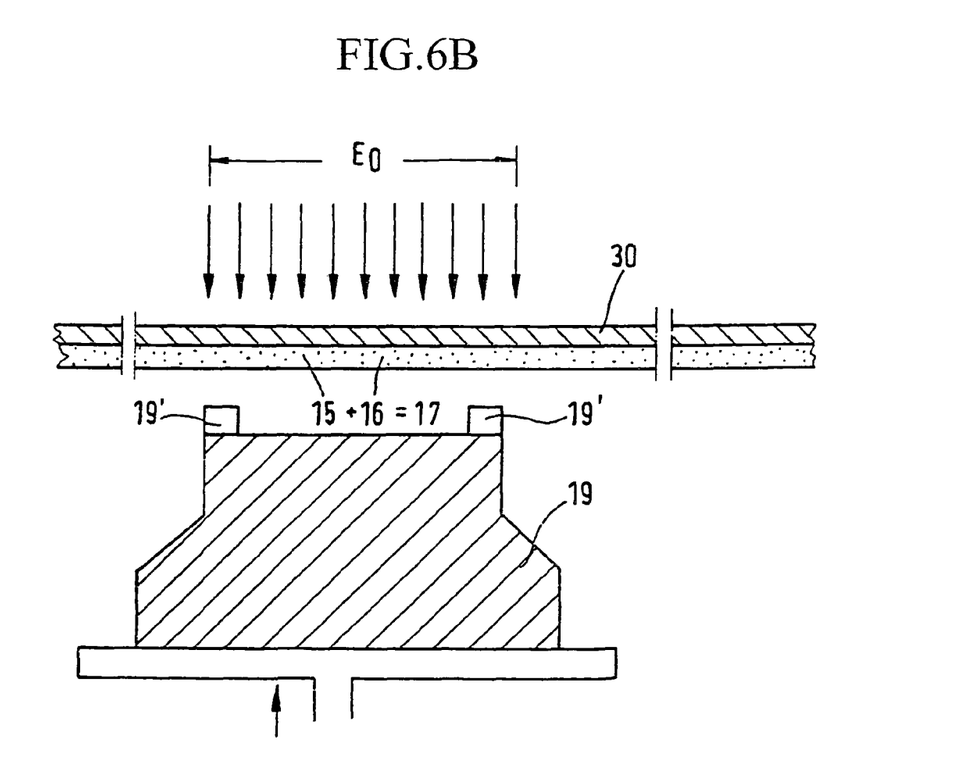

In further embodiments illustrated in FIGS. 5 and 6A and 6B, variations of a freeform fabrication system and process based on film transfer imaging technology are used for applying a principle of the present invention. In these embodiments, a belt 30, which may be provided in the form of an endless belt, is made of a transparent and/or flexible and/or resilient rubber/film/foil to provide thereon material 17 to be solidified. Material 17 to be solidified again contains filler substance 16 and a binder 15 and optionally further constituents as described above. The figures show certain stages within the entire fabrication process, where a part 19 of the final three-dimensional object had already been formed and placed on three-dimensional object carrier/support 20 embodied as a build platform. When a further layer of material shall be placed on top of object part 19, it is moved by an upward movement of carrier/support 20 to get in contact with the material 17 yet to be solidified. Once a contact is reached, electromagnetic radiation and/or synergistic stimulation is delivered in a pattern or an image with an associated basic energy density $E_0$ within the defined area of a building region (in this case a further layer to be solidified).

According to the embodiment illustrated by FIG. 5, energy density is varied by the super-exposure using an additional, second source of electromagnetic radiation and/or synergistic stimulation delivering or supplying further energy density $E_1$ in an inner region of the exposure pattern or image, thereby leaving a remaining basic (lower) energy density $E_0$ in the border region, in order to counter-act inhomogeneities caused by scattering phenomena of a ceramic filler substance in the boundary regions. First electromagnetic radiation and/or synergistic stimulation associated with $E_0$ and second electromagnetic radiation and/or synergistic stimulation associated with $E_1$ may have same or different wavelengths. The modified embodiments as already described in connection with FIG. 4, which can be used independent from the presence or absence of filler substance, can be applied to the embodiment of FIG. 5 as well.

In another embodiment as illustrated by FIGS. 6A and 6B, a principle of the present invention is explained when different building regions or different layers are used, or alternatively when different first and second materials are used for one or more building regions. In a particularly exemplified step illustrated by FIG. 6A, a modified second material 18 having no filler substance or another filler substance, different from the compositions 15, 16 or 17 of FIG. 5 described above, had been applied for forming a delicate boundary portion (for example a modified structure or an auxiliary support structure) at a building region by exposure to electromagnetic radiation and/or synergistic stimulation associated with a certain energy density $E_3$. After separation from belt 30, this belt 30 or another belt carrying again the first material 17 to be solidified and containing filler 16 and binder 15 is supplied. Upon a further contact by redirecting partial object (structure 19 plus 19') with a movement of its carrier/support 20 upwards and towards material 17, basic energy density $E_0$ varied relative to previous border region $E_3$ is exposed for the next building region or next layer for forming another part of the three-dimensional object. In this example, basic energy density $E_0$ is applied over the whole layer formed in FIG. 6B including its border region, but alternatively $E_0$ could be spatially separated into an energy density applied to the inner region and a lower energy density applied in the border region of the next layer as described before. As to a further alternative, instead of using different first and second materials 17 and 18 to be solidified, respectively, varied energy densities $E_3$ and $E_0$ may also be applied advantageously even with using the same materials to be solidified, the variation however being performed due to the quite different building region structure (delicate structure 19' and overlying layer formed over the whole cross-section of object 19).

Figure 7:
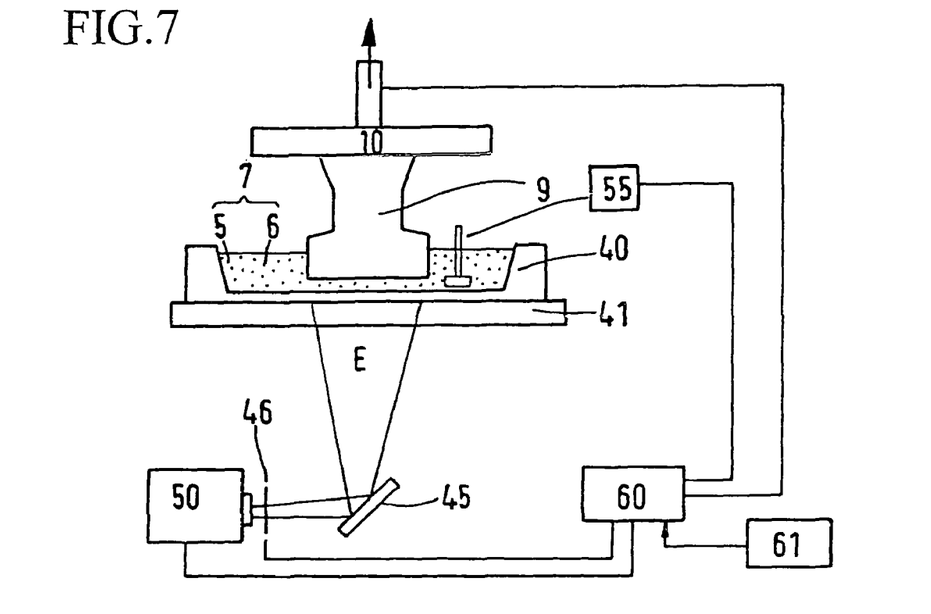
FIG. 7 schematically shows another embodiment of the present invention using a freeform fabrication system with a projection unit for selectively delivering electromagnetic radiation and/or synergistic stimulation, wherein energy density of is appropriately preset or adjusted depending on constitution and or characteristics of a material to be solidified containing a filler and a binder.
Figure 8:
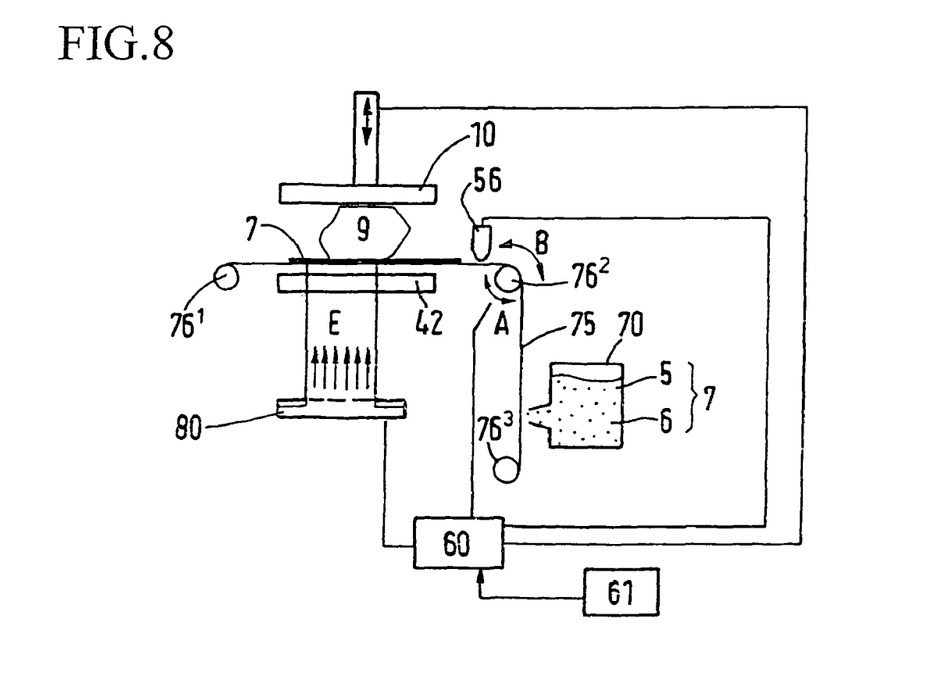
FIG. 8 schematically shows still another embodiment of the present invention using a freeform fabrication system using a film transfer technique and using a mask exposure unit for selectively delivering electromagnetic radiation and/or synergistic stimulation, wherein similar to the embodiment of FIG. 7 energy density of is appropriately preset or adjusted depending on constitution and or characteristics of a material to be solidified containing a filler and a binder.

In the embodiments schematically illustrated by FIGS. 7 and 8, the energy density of the electromagnetic radiation and/or synergistic stimulation delivery device as such can be respectively set or controlled by a previous setting or by a suitable control unit depending on at least one of the above mentioned criteria.

The embodiment shown in FIG. 7 again uses a material 7 to be solidified which contains at least binder 5 and filler 6 and which is contained in a vat, container or trough 40. The bottom of vat/container/trough 40 and a glass or plastic plate 41 used for its support is transparent to the type of electromagnetic radiation used. In this embodiment, electromagnetic radiation is projected from a projection unit 50 through a shutter 46 and via a reflector 45 to form a desired exposure image in or at the building region, to thereby solidify material 7 and to bind it to part 9 previously formed on the three-dimensional object carrier/support 10, which is again embodied as a build platform. In this manner a desired three-dimensional object can be successively formed either continuously or discontinuously, for example layer-wise with intermediate layer separations. A control unit embodied by a computer unit 60 serves to control operations of the freeform fabrication system at suitable locations, e.g. the projection unit 50 for variably tuning energy density E, the shutter 45 for opening and closing the path of the electromagnetic radiation, and the three-dimensional object carrier/support 10 for its movement (e.g. upward as indicated by an arrow) for enabling delivery of fresh material to be solidified. Here, the spatially controllable energy density E of the projection and exposure unit can be manually preset and input by a suitable control module 61 in advance of the building process, for example depending on the material used and known before (i.e. according to any one or a combination of parameters described above, such as type, particle size or amount of filler; type or amount of binder). Alternatively or in addition, energy density E can be manually and variably set and input into the control module 61, or is adjusted in-situ during the built program and built process depending on any one or a combination of parameters described above.

As a further possible option, a flowmeter or a viscosity meter (indicated by reference sign 55) may be provided if desired, allowing to measure in advance for a presetting operation, or to measure in situ during the building process either flowability or viscosity or both, in order to control the energy density E delivered by the projection unit 50 via control unit 60 depending on any one of flowability, viscosity and hardening rate of a material used for solidification (the latter in turn measurable by flowability and viscosity). Similar as described in the previous embodiments, the energy density E delivered by the projector 50 may be varied within the exposed area of the building region to be relatively high in the inner regions and relatively low in the border regions (i.e. by delivering spatially distinct energy densities $E_0$, $E_1$, etc.), in order to counteract scattering and/or reflection phenomena by the filler 6.

As a further modification of the embodiment of FIG. 6 it is possible to replace projector unit 50 and reflector 45 by a mask exposure system for the selective delivery of electromagnetic radiation and/or synergistic stimulation.

The embodiment shown in FIG. 8 illustrates a modification of the above embodiments for film transfer imaging techniques. Here, an embodiment of a freeform fabrication system according to the present invention uses a flexible and/or clear and/or resilient film/foil (respectively denoted by reference sign 75) conveying the material to be solidified 7. The material may contain at least binder 5 and filler 6. The film 75, which is here transparent to the electromagnetic radiation of interest at least in the built area, is adapted to transport material 7 to be solidified, which is dispensed from a solidifying material reservoir 70 onto one side of the film, from a supply station to the built area, to be subjected to radiation action in the desired building region through delivery of a prescribed energy density E. Transport may be carried out by an active roller $76^2$ under the control of control unit 60, while other rollers $76^1$ and $76^3$ may be passive and merely roll up remaining ends of flexible film 75. Further provided is a transparent glass or plastic plate 42 for providing support for flexible film 75 carrying the material 7 at the built area. This enhances the provision of a planar reference plane when desirable.

In this embodiment, the electromagnetic radiation and/or synergistic stimulation device is embodied by a mask exposure system comprising a bitmap generator and mask projector (commonly referred to by reference sign 80). By the mask exposure system (and optionally a further energy source not shown), energy density E is delivered selectively to the desired area of the building region in or at the reference plane. A control unit 60 is arranged to control the mask exposure system 80 for tuning energy density E, and may further control the whole system at suitable other locations, such as at the three-dimensional object carrier/support 10 for its movement (e.g. upward and downward as indicated by a double arrow) to enable steps of contacting fresh material 7 and of separation after solidification, at the opening of solidifying material reservoir 70 for the controlled dispensing of a fresh material film 7, etc. Similar to the embodiment of FIG. 7, the energy density E of the mask exposure system can be manually preset and input by a suitable control module 61 in advance of the building process, or alternatively or in addition, it can be adjusted in-situ during the built program and built process depending on any one or a combination of the factors described above. Like in the above embodiments, the energy density E delivered by the mask exposure system is varied by delivering spatially distinct energy densities $E_0$, $E_1$, etc.

Further modifications of the embodiments of FIGS. 7 and 8 are conceivable. For example it is possible to replace projector unit 50 and reflector 45 by a mask exposure system in FIG. 7, and vice versa to replace the mask exposure system 80 of FIG. 8 by another projection system, respectively for the selective delivery of electromagnetic radiation and/or synergistic stimulation.

The embodiments described above can be combined, and they can be modified while still applying the principles of the present invention. It is further noted that the present embodiments have been described for illustrative purposes only, while various further modifications and variations are possible and can be applied by the person skilled in the art within the scope and gist of the present invention.

The invention claimed is:

1. A process for producing at least one three-dimensional object, comprising:
   providing a material to be solidified;
   delivering electromagnetic radiation or synergistic stimulation in a pattern or an image to a building region for solidifying said material,
   wherein said delivering of electromagnetic radiation and/or synergistic stimulation is performed selectively to a defined area or volume of said material to be solidified; and
   controlling an energy density of electromagnetic radiation or synergistic stimulation in a border region of said pattern or image relative to a non-border region of said pattern or image based on an observed or determined degree of either out-shining of electromagnetic radiation or synergistic stimulation towards outside regions, or in-shining of electromagnetic radiation or synergistic stimulation into internal regions, respectively, across a border region or border regions of the three-dimensional object by adjusting an energy intensity of electromagnetic radiation or synergistic stimulation in the border region of said pattern or image relative to the non-border region of said pattern or image, wherein the step of adjusting the energy intensity of electromagnetic radiation or synergistic stimulation in the border region of said pattern or image relative to the non-border region of said pattern of image is dependent on at least one selected from:
   (a) intensity of electromagnetic radiation or synergistic stimulation delivered to said defined area or volume of said material to be solidified;
   (b) total shape or contour shape of said defined area or volume of said material to be solidified;
   (c) size of said defined area or volume of said material to be solidified; and
   (d) material to be solidified.

2. The process according to claim 1, wherein said controlling or adjustment, or said variation of the energy density in the border region(s) is performed only in one or more border regions, relative to normal non-border area regions/volume regions of the material to be solidified.

3. The process according to claim 1, further wherein the step of adjusting the energy intensity in the border region of said pattern or image relative to the non-border region of said pattern or image is dependent on at least one of following criteria, respectively applied alone or in combination:
(i) type, size or amount of filler contained in the material to be solidified;
(ii) type or amount of binder contained in the material to be solidified;
(iii) hardening rate, viscosity or flowability of the material to be solidified.

4. The process according to claim 1, wherein said material to be solidified comprises a ceramic particle filler.

5. The process according to claim 1, wherein said material to be solidified comprises a binder selected from the group consisting of photopolymers and adhesives.

6. The process according to claim 1, wherein said material to be solidified comprises a first binder substance and a second binder substance, and the first binder substance comprises a photocurable resin.

7. The process according to claim 1, wherein said step of controlling an energy density of electromagnetic radiation or synergistic stimulation in a border region of said pattern or image relative to a non-border region of said pattern or image is performed by reference to a standard energy density being defined by any characteristic selected from a reference intensity, a reference total shape, a reference contour shape, a reference size and a reference material, and by adjusting the actual energy density delivered to the border region(s) depending on a variation of actual built data or actual built object relative to said referenced characteristic.

8. The process according to claim 1, wherein said step of controlling an energy density of electromagnetic radiation or synergistic stimulation in a border region of said pattern or image relative to a non-border region of said pattern or image is performed by reference to a standard energy density being defined by a reference object having a polygonal cross-sectional shape and having linear contour lines, and wherein the adjustment is carried out based on variations in terms of convex or concave border contours in the border regions of the actual built data or actual built object.

9. The process according to claim 1, wherein said step of controlling an energy density of electromagnetic radiation or synergistic stimulation in a border region of said pattern or image relative to a non-border region of said pattern or image is performed by reference to a standard energy density being defined by a reference material to be solidified, and wherein the adjustment is carried out based on a variation relative to the actually used material to be solidified.

10. The process according to claim 1, wherein said selective delivery of electromagnetic radiation or synergistic stimulation comprises using a mask projector or a projection unit to deliver the electromagnetic radiation or synergistic stimulation selectively to the defined area or volume of material to be solidified.

11. The process according to claim 1, wherein said selective delivery of electromagnetic radiation or synergistic stimulation is based on an imaging unit comprising a predetermined number of discrete imaging elements or pixels; and wherein the step of adjusting an energy intensity of electromagnetic radiation in the border region of said pattern or image relative to the non-border region of said pattern or image comprises adjusting gray values or color values allocated to at least a part of the pixels covering at least the border region.

12. The process according to claim 1, wherein said selective delivery of electromagnetic radiation or synergistic stimulation is based on an imaging unit comprising a predetermined number of discrete imaging elements or pixels; and wherein the energy density is controlled in one or more bitmap masks which is (are) generated "on the fly".

13. The process according to claim 1, wherein the three-dimensional object is built on an object carrier or support, wherein said object carrier or support is moved upward as the built three-dimensional object grows.

14. The process according to claim 1, wherein the material to be solidified is provided in the building region on a transparent film at the stage of delivering electromagnetic radiation or synergistic stimulation.

15. The process according to claim 1, wherein the material to be solidified is conveyed from a resin source to the building region on a movable film.

16. The process according to claim 15, wherein a mask projector is disposed below the film to project an image through the film.

17. The process according to claim 16, wherein the mask projector is a digital light projector.

18. The process according to claim 1, wherein the three-dimensional object is built on a object carrier or support placed above a device for delivering electromagnetic radiation or synergistic stimulation, and a transparent plate is disposed between said transparent object carrier or support and said radiation or synergistic stimulation delivery device.

* * * * *